United States Patent

Mendoza et al.

[19]

[11] Patent Number: 5,984,654
[45] Date of Patent: Nov. 16, 1999

[54] COMPRESSED AIR DRIVEN DISPOSABLE HAND TOOL HAVING A ROTOR WITH RADIALLY MOVING VANES

[75] Inventors: Jose L. Mendoza, Rancho Cordova; Philip Theodore Lingman, Cotati, both of Calif.

[73] Assignee: Denticator International, Inc., Earth City, Mo.

[21] Appl. No.: 08/979,538

[22] Filed: Nov. 26, 1997

Related U.S. Application Data

[63] Continuation of application No. 08/479,929, Jun. 7, 1995, Pat. No. 5,743,718.

[51] Int. Cl.⁶ ................................................ F03C 2/00
[52] U.S. Cl. ...................... 418/236; 418/266; 415/141; 415/904; 433/132
[58] Field of Search ..................................... 418/225, 227, 418/259, 266, 236; 415/141, 904; 433/132

[56] References Cited

U.S. PATENT DOCUMENTS

| Re. 24,391 | 11/1957 | McFadden | 51/170 |
|---|---|---|---|
| 263,814 | 9/1882 | Schmitz . | |
| 969,378 | 9/1910 | Krause . | |
| 1,343,115 | 6/1920 | Current . | |
| 1,601,397 | 9/1926 | Kochendarfer . | |
| 1,999,488 | 4/1935 | Swisher et al. | 32/27 |
| 2,017,881 | 10/1935 | Wiseman | 32/59 |
| 2,025,779 | 12/1935 | Roelke | 32/11 |
| 2,033,662 | 3/1936 | Witt . | |
| 2,128,157 | 8/1938 | Monnier et al. | 253/2 |
| 2,135,933 | 11/1938 | Blair | 128/48 |
| 2,203,974 | 6/1940 | Weinhardt . | |
| 2,226,145 | 12/1940 | Smith | 15/29 |

(List continued on next page.)

FOREIGN PATENT DOCUMENTS

| 646193 | 6/1937 | Germany . | |
|---|---|---|---|
| 803306 | 7/1949 | Germany . | |
| 102433 | 5/1951 | New Zealand . | |
| 12584 | 3/1903 | Sweden . | |
| 2154283 | 9/1985 | United Kingdom . | |
| 2209284 | 5/1989 | United Kingdom | A61C 1/05 |

OTHER PUBLICATIONS

Denticator; product brochure; 1990; entire brochure.

Oralsafe; Advertisement for Oralsafe Disposable Handpiece; Dentistry Today Trade Journal; Aug., 1992; entire advertisement.

SmartPractice; Advertisement for a small angle prophy angle; entire advertisement, Date Unknown.

Dental Products Report; "Disposable Handpice", Nov. 1992, p. 96.

(List continued on next page.)

*Primary Examiner*—Charles G. Freay
*Attorney, Agent, or Firm*—Polster, Lieder, Woodruff & Lucchesi

[57] ABSTRACT

A fluid reaction device (10) is provided having a rotor (90) with vanes (92) pivotably connected thereto. The device (10) includes an entrance (30) for elevated pressure fluid and an outlet (40) for discharge of the fluid after contacting the rotor (90). The elevated pressure fluid passes from the entrance (30) into a high pressure area. The high pressure area is in contact with inlet ports (74) accessing a cylinder (70) within the device (10). The cylinder (70) supports the rotor (90) with a rotational axis (M) of the rotor (90) off center with respect to a central axis (N) of the cylinder (72). The elevated pressure fluid causes the rotor (90) and an attached output shaft (97) to rotate. The rotor (90) includes a trunk (24) with a plurality of posts (93) extending therefrom and with vanes (92) connected to the posts (93) through hinges (94). The vanes (92) can pivot from a first position collapsed against the trunk (24) to a second position spaced away from the trunk (24). The vanes (92) thus can contact a cylindrical wall of the cylinder (70) while the rotor (90) rotates. Exhaust ports (76) are spaced from the inlet ports (74) and provide communication with a low pressure area which exhausts low pressure fluid to the outlet (40).

11 Claims, 4 Drawing Sheets

U.S. PATENT DOCUMENTS

| | | | |
|---|---|---|---|
| 2,300,828 | 11/1942 | Goldenberg | 32/59 |
| 2,315,016 | 3/1943 | Shotton | 32/26 |
| 2,328,270 | 8/1943 | Greenberg | 74/56 |
| 2,463,118 | 3/1949 | Moore | 103/140 |
| 2,586,968 | 2/1952 | Maclay . | |
| 2,684,035 | 7/1954 | Kemp . | |
| 2,789,352 | 4/1957 | Wiseman | 32/59 |
| 2,836,877 | 6/1958 | Hannahan . | |
| 2,933,046 | 4/1960 | McCray . | |
| 2,937,444 | 5/1960 | Kern | 32/27 |
| 3,043,274 | 7/1962 | Quackenbush | 121/36 |
| 3,054,355 | 9/1962 | Neely . | |
| 3,163,934 | 1/1965 | Wiseman | 32/27 |
| 3,192,922 | 7/1965 | Winkler | 128/62 |
| 3,229,369 | 1/1966 | Hoffmeister et al. | 32/27 |
| 3,309,965 | 3/1967 | Weickgenannt . | |
| 3,376,825 | 4/1968 | Burnett | 103/136 |
| 3,421,224 | 1/1969 | Brehm et al. | 32/27 |
| 3,477,793 | 11/1969 | Kitagawa . | |
| 3,510,229 | 5/1970 | Smith | 415/141 |
| 3,719,440 | 3/1973 | Snider . | |
| 3,727,313 | 4/1973 | Graham | 32/27 |
| 3,740,853 | 6/1973 | Brahler | 32/59 |
| 3,855,704 | 12/1974 | Booth | 32/28 |
| 3,856,432 | 12/1974 | Campagnuolo et al. | 416/45 |
| 3,877,574 | 4/1975 | Killick | 206/368 |
| 3,942,392 | 3/1976 | Page, Jr. et al. . | |
| 3,955,284 | 5/1976 | Balson | 32/27 |
| 3,987,550 | 10/1976 | Danne et al. | 32/59 |
| 4,040,311 | 8/1977 | Page, Jr. et al. . | |
| 4,053,983 | 10/1977 | Flatland | 32/27 |
| 4,171,571 | 10/1979 | Gritter | 32/26 |
| 4,182,041 | 1/1980 | Girard | 433/115 |
| 4,185,386 | 1/1980 | Nordin et al. . | |
| 4,248,589 | 2/1981 | Lewis | 433/80 |
| 4,259,071 | 3/1981 | Warden et al. | 433/166 |
| 4,261,536 | 4/1981 | Melcher et al. | 244/155 A |
| 4,266,933 | 5/1981 | Warden et al. | 433/82 |
| 4,365,956 | 12/1982 | Bailey | 433/115 |
| 4,392,779 | 7/1983 | Bloemers et al. . | |
| 4,465,443 | 8/1984 | Karden | 418/43 |
| 4,540,337 | 9/1985 | Olsen . | |
| 4,693,871 | 9/1987 | Geller | 433/116 |
| 4,767,277 | 8/1988 | Buse | 416/241 A |
| 4,795,343 | 1/1989 | Choisser | 433/116 |
| 4,842,516 | 6/1989 | Choisser | 433/132 |
| 4,846,638 | 7/1989 | Pahl et al. . | |
| 4,863,344 | 9/1989 | Stefanini | 415/141 |
| 4,929,180 | 5/1990 | Moreschini | 433/166 |
| 4,941,828 | 7/1990 | Kimura | 433/114 |
| 5,020,994 | 6/1991 | Huang | 433/126 |
| 5,028,233 | 7/1991 | Witherby | 433/125 |
| 5,040,978 | 8/1991 | Falcon et al. | 433/125 |
| 5,062,796 | 11/1991 | Rosenberg | 433/82 |
| 5,094,615 | 3/1992 | Bailey | 433/88 |
| 5,120,220 | 6/1992 | Butler | 433/125 |
| 5,156,547 | 10/1992 | Bailey | 433/125 |
| 5,163,825 | 11/1992 | Oetting . | |
| 5,423,679 | 6/1995 | Bailey . | |
| 5,425,634 | 6/1995 | Brockway . | |
| 5,425,638 | 6/1995 | Abbott . | |
| 5,484,284 | 1/1996 | Bailey . | |
| 5,503,555 | 4/1996 | Bailey . | |
| 5,667,383 | 9/1997 | Mendoza et al. | 433/114 |

OTHER PUBLICATIONS

Diversified Dental Supply, Inc., advertisement for disposable high speed hand pieces, entire ad Date Unknown.

The National Magazine for Dental Hygiene Professionals, Product Report, "Prophy Cups", Jan., 1992, p. 38.

Dental Products Report, New Products, "Prophy Cup", Jan. 1992, pae 30.

Oralsafe; Advertisement for Oralsafe disposable handpieces; Impact, The Newsmagazine of the Academy of General Dentisrty, Dec., 1992; entire advertisement.

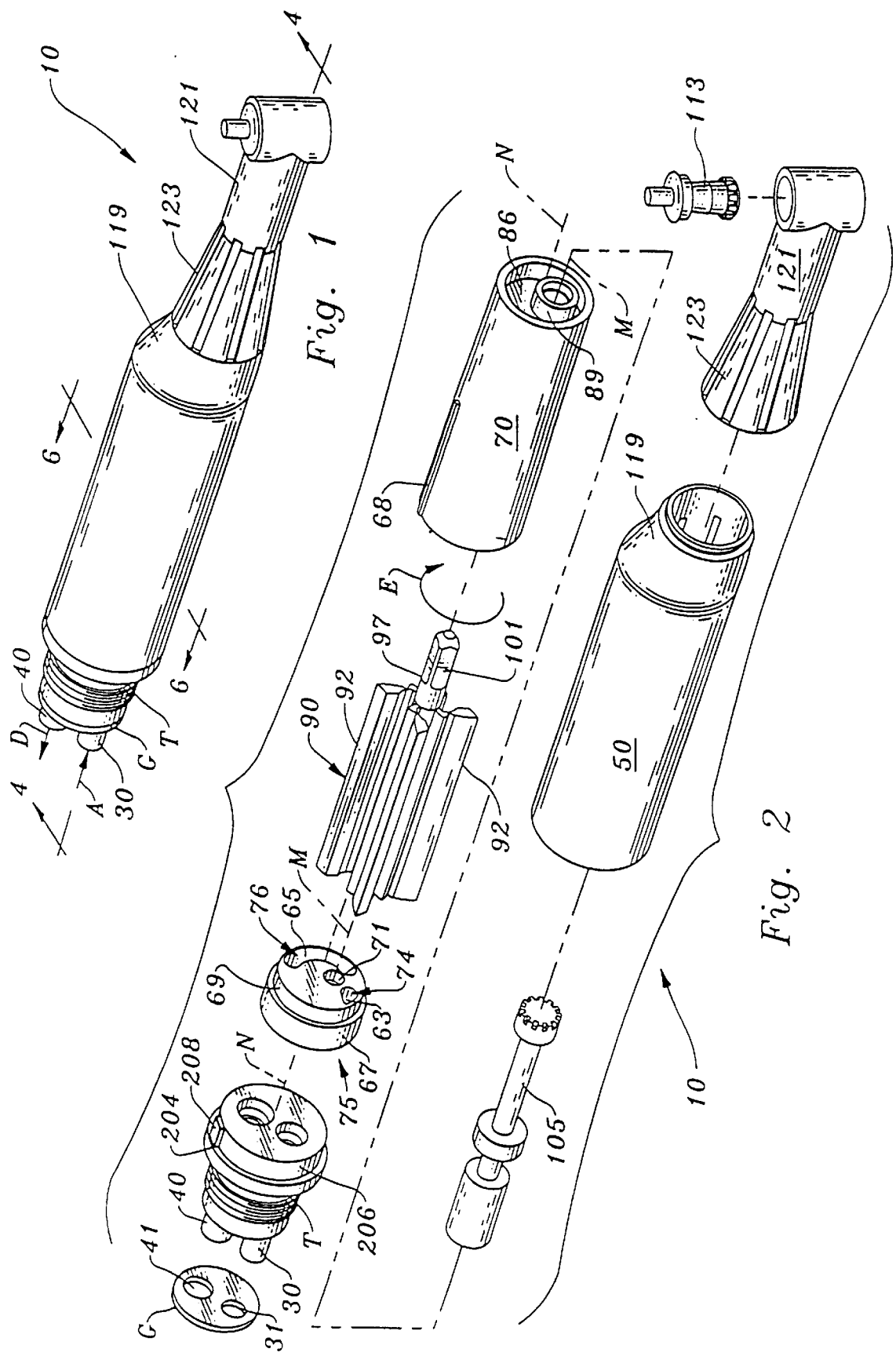

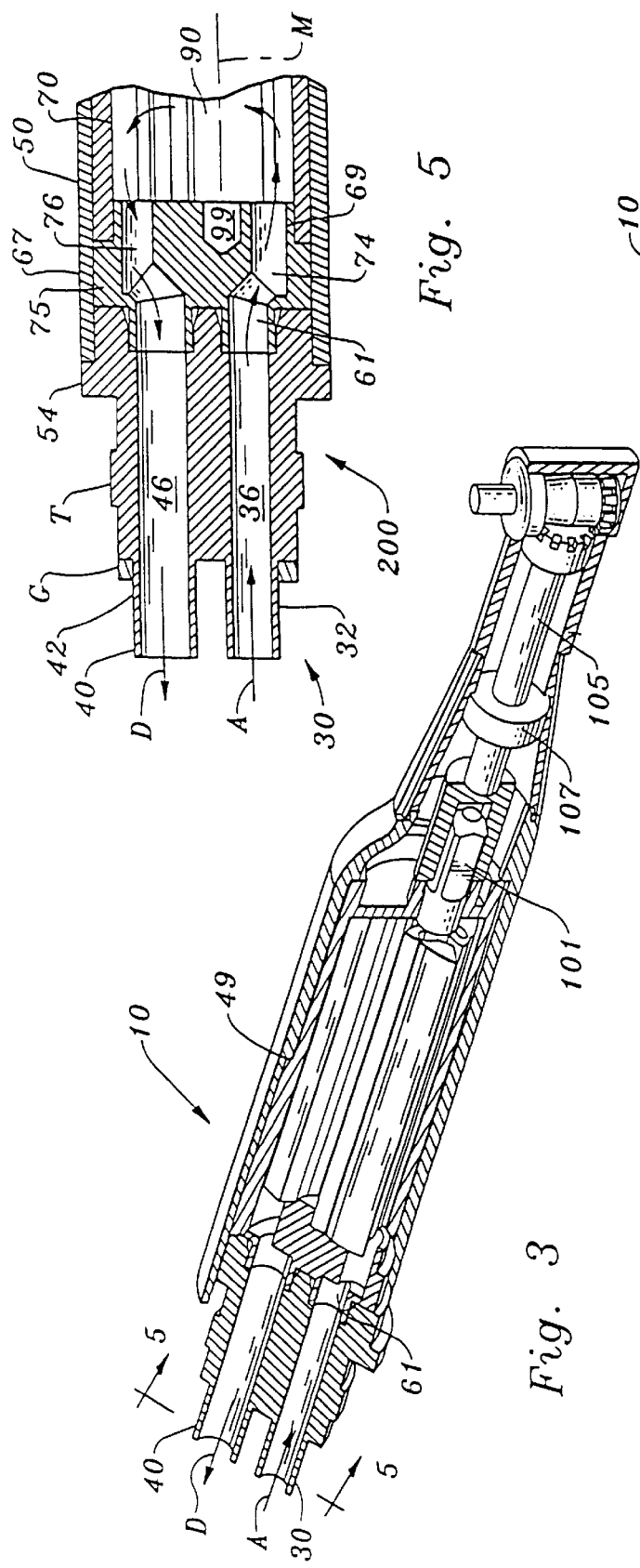

COMPRESSED AIR DRIVEN DISPOSABLE HAND TOOL HAVING A ROTOR WITH RADIALLY MOVING VANES

CROSS REFERENCE TO RELATED APPLICATIONS

This application is a continuation of application number 08/479,929, filed Jun. 7, 1995, now U.S. Pat. No. 5,743,718.

This application is related to application Ser. No. 08/294,621 filed on Aug. 23, 1994 now U.S. Pat. No. 5,667,773.

FIELD OF THE INVENTION

This invention generally relates to motors and fluid reaction devices which utilize elevated pressure gases or liquids to generate rotational shaft output. More specifically, this invention relates to hand held fluid driven motors with high torque and relatively low speed when unloaded and including rotors with dynamic vanes which move relative to the rotor.

BACKGROUND OF THE INVENTION

Fluid driven motors are known in the art which utilize elevated pressure or elevated velocity gases, such as air, to cause a shaft to rotate so that work can be done. Some prior art devices date back to around 1873, when steam power systems were being developed. In general, the high velocity fluid driven motors include a fixed vane rotor and a fixed vane stator. A nozzle directs the high velocity air against the fixed vanes of the rotor, causing rotor rotation. Such fixed rotor fluid driven motors generally exhibit extremely high free speeds, speeds exhibited when no load is placed on the motor, especially when sized to be hand held.

Many different types of fluid motors are known in the art that have been used with many different liquids and gases, including steam, compressed air and water. One type converts a high velocity stream of fluid (kinetic energy type) into mechanical rotation. These range from large water turbines that are used in hydroelectric generating plants and aircraft jet engines to very small dental drills that are used in filling teeth. The speed of a turbine dental drill ranges from 500,000 to a million RPM, and produces a very low torque. The jet engine typically turns at approximately 25,000 RPM and produces a high torque by having many stages of redirection of the gas stream and many expansion stages.

Another common type of motor uses static fluids under pressure to produce mechanical motion (potential energy type). Typical motors of this type use pressure against pistons to produce motion. Examples of this type include automobile engines and steam locomotives. Another type of static fluid pressure motor does not require a crank or similar mechanism to convert the fluid pressure to shaft rotation. In these motors, often referred to as a vane type, the pressure is applied directly against the vanes, which are coupled to the shaft. In contrast to pistons which have a fixed area exposed to the fluid pressure, the well known vane motor presents an area that ranges from zero to a maximum, in half of a revolution.

These prior art rotors which rely on static fluid pressure include a dynamic rotor having flat vanes which slide away from and toward a geometric center of the rotor. The rotor is located asymmetrically within a cylinder such that air passing from an inlet to an outlet within the cylinder causes the rotor to rotate in only one direction. The vanes slide away from and toward a rotational axis of the rotor as the rotor rotates. Because such sliding flat vane rotors contact a wall of the cylinder, friction exists which determines a maximum free speed of the rotor for a given air pressure. Such motors also exhibit relatively high torque at lower speeds than high velocity air motors.

While such sliding flat vane rotors are useful for many applications, some applications require higher torque at still lower speeds than those obtainable with flat sliding vane rotors. bearing the output shaft to obtain desired speeds is often excessively complex or expensive for many applications. The sliding vanes are also constrained geometrically to exhibit only slight extension, to prevent excessive shear stress on the vanes. Additionally, flat sliding vane rotors require some form of system to extend the vanes away from the rotor at start up, before centrifugal forces can be utilized to maintain the vanes against a surrounding cylindrical wall. The fluid pressure does not inherently cause the vanes to extend. Finally, such flat sliding vane rotors must be formed with multiple pieces and to precise tolerances to ensure that the vanes can effectively slide within slots in the rotor. Accordingly, a need exists for a fluid driven motor or fluid reaction device which has high torque at low speeds but which is sufficiently easily manufactured to facilitate economical disposability and has vanes which extend readily when the device is started. Additionally, a need exists for a fluid reaction device which has a high torque at low speeds without the use of gears.

The following prior art reflects the state of the art of which applicant is aware and is included herewith to discharge applicant's acknowledged duty to disclose relevant prior art. However, it is respectfully submitted that none of these prior art devices teach singly, nor render obvious when considered in any conceivable combination, the nexus of the instant invention as especially claimed hereinafter.

| INVENTOR | PATENT NO. | ISSUE DATE |
| --- | --- | --- |
| Schmitz | 263,814 | September 5, 1882 |
| Current | 1,343,115 | June 8, 1920 |
| Kochendarfer | 1,601,397 | September 28, 1926 |
| Swisher, et al | 1,999,488 | April 30, 1935 |
| Wiseman | 2,017,881 | October 22, 1935 |
| Roelke | 2,025,779 | December 31, 1935 |
| Monnier, et al. | 2,128,157 | August 23, 1938 |
| Blair | 2,135,933 | November 8, 1938 |
| Smith | 2,226,145 | December 24, 1940 |
| Goldenberg | 2,300,828 | November 3, 1942 |
| Shotton | 2,315,016 | March 30, 1943 |
| Greenberg | 2,328,270 | August 31, 1943 |
| Moore | 2,463,118 | March 1, 1949 |
| Wiseman | 2,789,352 | April 23, 1957 |
| McFadden | Re. 24,391 | November 12, 1957 |
| Kern | 2,937,444 | May 24, 1960 |
| Quackenbush | 3,043,274 | July 10, 1962 |
| Wiseman | 3,163,934 | January 5, 1965 |
| Winkler | 3,192,922 | July 6, 1965 |
| Hoffmeister, et al. | 3,229,369 | January 18, 1966 |
| Burnett | 3,376,825 | April 9, 1968 |
| Brehm, et al. | 3,421,224 | January 14, 1969 |
| Smith | 3,510,229 | May 5, 1970 |
| Graham | 3,727,313 | April 17, 1973 |
| Brahler | 3,740,853 | June 26, 1973 |
| Booth | 3,855,704 | December 24, 1974 |
| Campagnuolo, et al. | 3,856,432 | December 24, 1974 |
| Killick | 3,877,574 | April 15, 1975 |
| Balson | 3,955,284 | May 11, 1976 |
| Danne, et al. | 3,987,550 | October 26, 1976 |
| Flatland | 4,053,983 | October 18, 1977 |
| Gritter | 4,1,71,571 | October 23, 1979 |
| Girard | 4,182,041 | January 8, 1980 |
| Lewis | 4,248,589 | February 3, 1981 |
| Warden et al. | 4,259,071 | March 31, 1981 |

-continued

| | | |
|---|---|---|
| Melcher | 4,261,536 | April 14, 1981 |
| Warden et al. | 4,266,933 | May 12, 1981 |
| Bailey | 4,365,956 | December 28, 1982 |
| Karden | 4,465,443 | August 14, 1984 |
| Geller | 4,693,871 | September 15, 1987 |
| Buse | 4,767,277 | August 30, 1988 |
| Choisser | 4,795,343 | January 3, 1989 |
| Choisser | 4,842,516 | June 27, 1989 |
| Stefanini | 4,863,344 | September 5, 1989 |
| Moreschini | 4,929,180 | May 29, 1990 |
| Kimura | 4,941,828 | July 17, 1990 |
| Huang | 5,020,994 | June 4, 1991 |
| Witherby | 5,028,233 | July 2, 1991 |
| Falcon et al. | 5,040,978 | August 20, 1991 |
| Rosenberg | 5,062,796 | November 5, 1991 |
| Bailey | 5,094,615 | March 10, 1992 |
| Butler | 5,120,220 | June 9, 1992 |
| Bailey | 5,156,547 | October 20, 1992 |

FOREIGN PATENT DOCUMENTS

| DOCUMENT NUMBER | DATE | NAME | CLASS | SUB-CLASS* | FILING DATE |
|---|---|---|---|---|---|
| 12584 (Sweden) | 03/1903 | Munson | 418 | 225 | |
| 646,193 (Germany) | 06/1937 | Dürhager | 30b | 202 | 5/1937 |
| 803,306 (Germany) | 07/1949 | Hollmann | 418 | 225 | |
| 102,433 (New Zealand) | 05/1951 | Callaghan | 433 | 132 | |
| GB 2 209 284-A | 05/1989 | Kalsha | A61C | 1/05 | 07/1988 |

OTHER PRIOR ART (Including Author, Title, Date, Pertinent Pages, Etc.)

Denticator; Product Brochure; 1990; entire brochure.
Oralsafe; Advertisement for Oralsafe Disposable Handpiece; Dentistry Today Trade Journal; August, 1992; entire advertisement.
SmartPractice; Advertisement for a smart angle prophy angle; entire advertisement.
Dental Products Report, "Disposable Handpiece", November 1992, page 96.
Diversified Dental Supply, Inc., Advertisement for Disposable High Speed Hand Pieces, entire advertisement.
The National Magazine for Dental Hygiene Professionals, Product Report, "Prophy Cups", January 1992, page 38.
Dental Products Report, New Products, "Prophy Cups", January 1992, page 30.
Oralsafe; Advertisement for Oralsafe disposable handpieces; Impact, The Newsmagazine of the Academy of General Dentistry, December 1992; entire advertisement.

The patent to Smith teaches a one-way pump with an impeller having blades connected to the impeller through a flexible web portion which allows the blades to be pivoted in one direction but not the other. The present invention is distinguishable from Smith for several reasons. Inter alia, shaft power is provided for an output shaft instead of pumping fluid through a system. Also, the vanes of this invention contact a cylinder wall and the rotor of this invention is offset within the cylinder within which it resides.

The patent to Stefaninii teaches a centrifugal pump having impeller blades which are pivoted to rotate between two extreme positions. The present invention is distinguishable from the pump taught by Stefanini in that, inter alia, the present invention provides a fluid reaction device producing shaft rotation instead of fluid pumping. Also, the vanes of this invention contact a cylindrical wall surrounding the vanes, and the rotor of this invention is oriented offset with respect to a center of the cylinder within which it rotates.

The remainder of the prior art diverge even more starkly from the present invention than the prior art specifically distinguished above.

SUMMARY OF THE INVENTION

The fluid reaction device of this invention utilizes fluid, such as air under elevated pressure, to cause a shaft to rotate and do useful work. The device includes a rotor with vanes extending therefrom. The rotor is coupled to an output shaft. The rotor is supported within a cavity which allows rotation of the rotor therein. A plurality of inlet exhaust ports pass into the cavity to allow fluid under elevated pressure to enter the cavity and reduced pressure fluid to exit the cavity. The inlet port is coupled to a source of elevated pressure fluid.

The rotor is supported so that a rotational axis of the rotor is spaced from a central axis of symmetry of the cavity Thus, the rotor is oriented off-center within the cavity. The vanes of the rotor are pivotably attached to the rotor such that the vanes can contact the cavity wall at all times by pivoting away from and toward the rotor as the rotor rotates. The pivoting vanes deter fluid from passing around the rotor without rotor rotation. The pivoting vanes also generate friction for the rotor, acting as a governor by keeping the rotor from exceeding a maximum free speed for the device. The pivoting vanes are entirely exposed to the driving fluid, maximizing a reaction surface for the high energy fluid. The pivoting vanes provide the rotor with a greater radius on one side of the rotor than on an opposite of the rotor. This difference increases a torque imparted by the rotor to the output shaft. In one form of the invention, the inlet exhaust ports enter the cavity at an end thereof substantially parallel to an axis of rotation of the rotor.

OBJECTS OF THE INVENTION

Accordingly, it is a primary object of the present invention to provide a fluid reaction device having low speed and high torque characteristics.

It is another object of the present invention to provide a fluid reaction device including a rotor which is caused to rotate by elevated pneumatic fluid pressure.

It is another object of the present invention to provide a fluid reaction device which is self-starting.

Another object of the present invention is to provide a fluid reaction device having a rotor formed from low cost easily machined materials.

Another object of the present invention is to provide a fluid reaction device formed from injection moldable plastic materials.

Another object of the present invention is to provide a fluid reaction device which can produce torque without rotation.

It is another object of the present invention to provide a fluid reaction device that is easy to make and assemble.

Another object of the present invention is to provide a fluid reaction device including a rotor with vanes which contact a wall surrounding the cavity without requiring precise dimensional tolerances for the vanes.

It is another object of the present invention to provide a fluid reaction device having a rotor with vanes which pivot with respect to a trunk of the rotor.

Another object of the present invention is to provide a fluid reaction device which minimizes cooling by inhibiting significant adiabatic expansion of drive fluid utilized therein.

It is another object of the present invention to provide a fluid reaction device having a rotor with a trunk, hinges and vanes which are preferably all formed integrally together, but can be formed separately.

Another object of the present invention is to provide a fluid reaction device with a rotor having vanes which have a first position adjacent a trunk of the rotor and a second position spaced from a trunk of the rotor manufactured to be biased toward the second position.

Another object of the present invention is to provide a fluid reaction device having a substantially constant free speed when unloaded and powered with a constant fluid pressure differential.

Another object of the present invention is to provide an alternative to the air motor featuring a rotor with radially sliding vanes by providing a fluid reaction device featuring a rotor with pivoting vanes.

Another object of the present invention is to provide a device which can be manufactured in a sufficiently economical manner to facilitate disposal after limited use.

Another object of the present invention is to provide a fluid reaction device which is lightweight and can be held in the hand of a user.

It is another object of the present invention to provide a fluid reaction device which delivers high power and high torque with a small diameter.

Another object of the present invention is to provide a fluid reaction device with a rotor oriented offset within a cavity to increase a torque produced by the rotor.

Viewed from a first vantage point it is the object of the present invention to provide a hand tool device receiving fluid as input and having a rotating shaft as output, comprising in combination: a rotor including a substantially rigid trunk, a plurality of vanes, and a means to pivotably attach said vanes to said trunk; a hollow cavity, said cavity including means to inlet fluid into said cavity, parallel to an axis of rotor rotation means to exhaust fluid out of said cavity, and means to rotatably support said trunk of said rotor within said cavity; and an output shaft coupled to said rotor such that when fluid enters said cavity, said shaft is caused to rotate.

Viewed from a second vantage point it is the object of the present invention to provide a method for utilizing fluid to cause a shaft to rotate, including the steps of: forming a rotor to include a trunk and a plurality of vanes, connecting each vane through a hinge to the trunk, the hinge allowing each said vane to pivot with respect to the trunk between a first collapsed position and a second extended position, orienting the rotor within a hollow cavity, providing an inlet fluid port passing into the cavity, providing an outlet fluid port passing into the cavity parallel to an axis of rotor rotation means, coupling the rotor to a means to extract rotational energy from the rotor, coupling the inlet fluid port to a source of fluid, and directing fluid from the source of fluid through the inlet fluid ports and into contact with the vanes of the rotor, causing the rotor to rotate.

Viewed from a third vantage point it is the object of the present invention to provide a hand tool device having a substantially constant velocity rotational output comprising in combination: a rotor having a trunk, vanes and hinge means between said trunk and said vanes to pivot said vanes between a first position and a second position, a wall surrounding said rotor, said first position defined by said vanes collapsed adjacent said trunk with a portion of said vanes abutting said wall, said second position defined by said vanes pivoted away from said trunk with a portion of said vanes abutting said wall, an inlet passing through an end of said wall coupled to a source fluid, and an outlet passing through an end of said wall.

Viewed from a fourth vantage point it is the object of the present invention to provide a hand tool device for converting elevated energy drive fluid into lower energy drive fluid and rotational power output, comprising in combination: a cavity having a fluid inlet and a fluid outlet, a rotor, means to rotatably support said rotor within said cavity, and vanes attached to said rotor and extending from said rotor, said vanes including a surface exposed to the drive fluid at all times, and a swivel means on a housing of said hand tool device to allow relative rotation of a portion of the housing thereabout, parallel to an axis of rotation of said rotor.

These and other objects will be made manifest when considering the following detailed specification when taken in conjunction with the appended drawing figures.

BRIEF DESCRIPTION OF THE DRAWINGS

FIG. 1 is a perspective view of the hand tool device of this invention as assembled.

FIG. 2 is a perspective exploded parts view of this invention with individual parts separated according to an order of assembly.

FIG. 3 is a perspective view of that which is shown in FIG. 1 with portions thereof cut away to reveal interior details such as how the fluid passes through the device.

FIG. 4 is a sectional view taken along line 4—4 of FIG. 1.

FIG. 5 is a sectional view taken along line 5—5 of FIG. 3.

DESCRIPTION OF PREFERRED EMBODIMENTS

Figure 6:
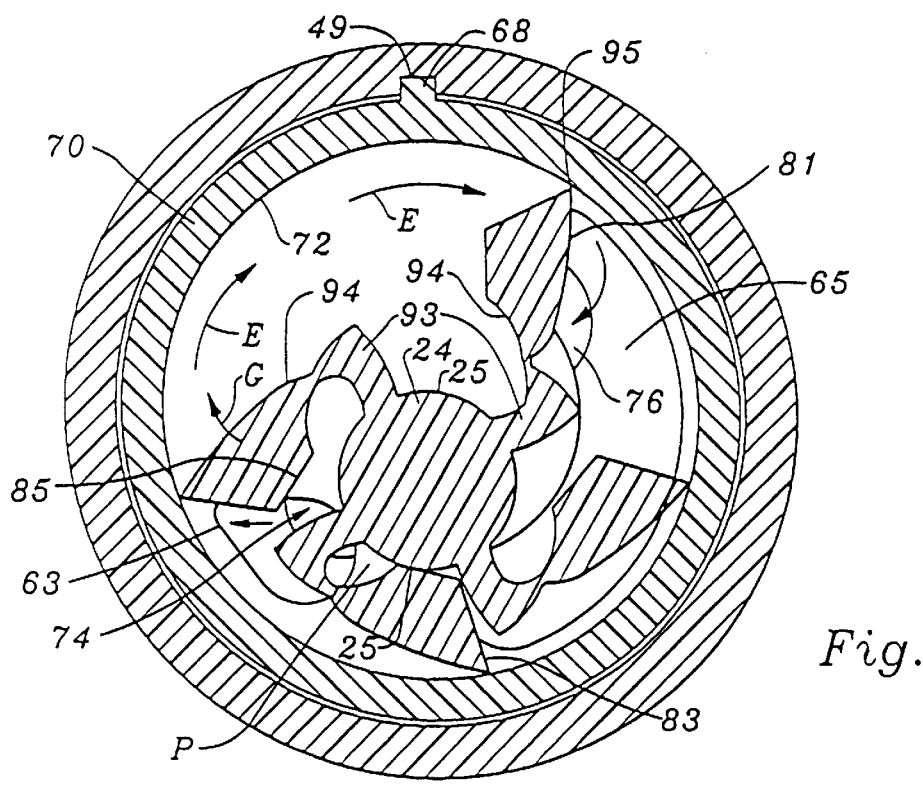
FIG. 6 is a sectional view taken along lines 6—6 of FIG. 1.
Figure 7:
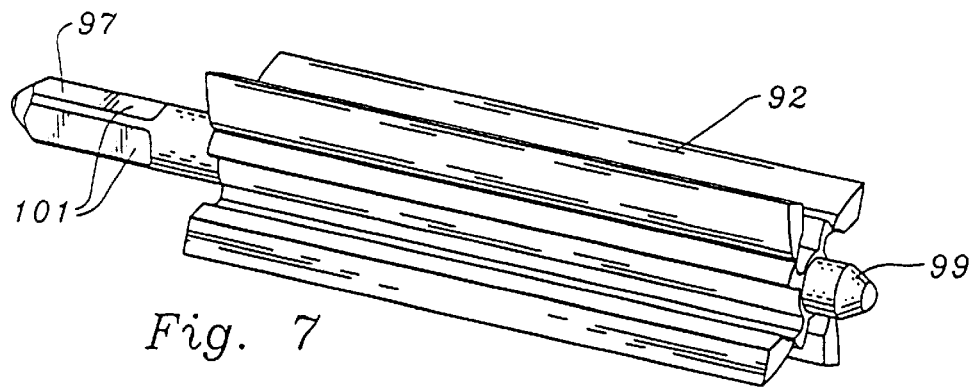
FIG. 7 is a perspective view of a rotor of this invention.
Figures 8, 9:
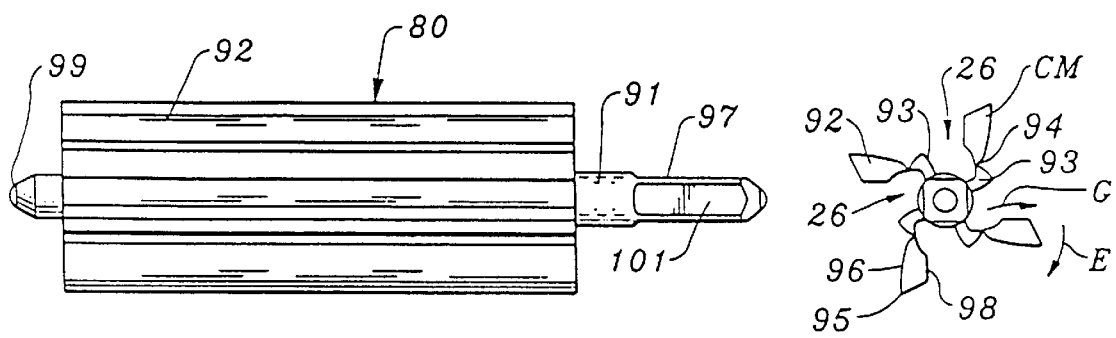
FIG. 8 is a side view of the rotor of FIG. 7.
FIG. 9 is a front view of that which is shown in FIG. 8.
Figure 10A:
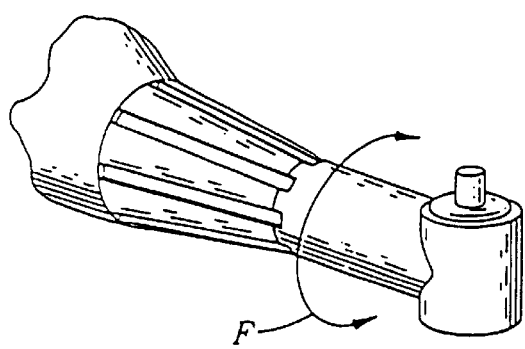
FIGS. 10A–10D are perspective views of a housing portion of this invention, showing a swivel.
Figure 10B:
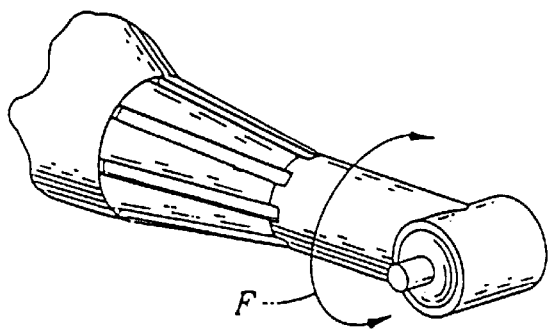
Figure 10C:
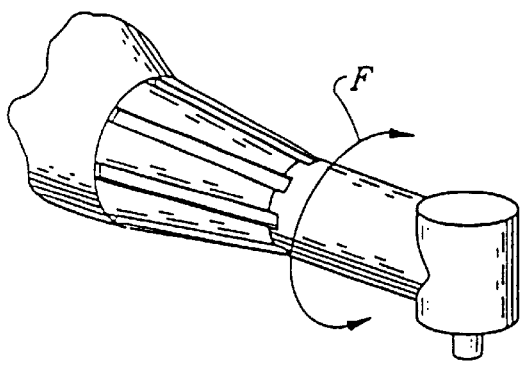
Figure 10D:
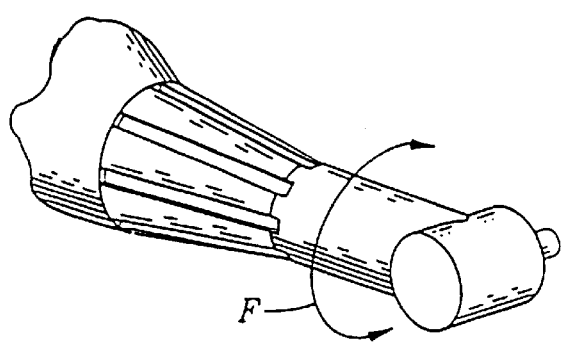
Figure 11:
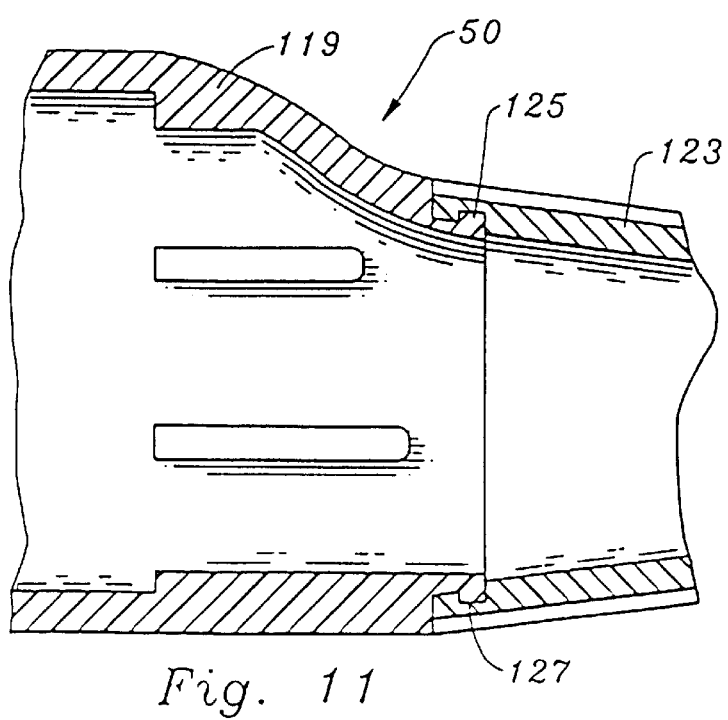
FIG. 11 is a sectional view the swivel detail shown in FIG. 10.

Referring to the drawings, wherein like reference numerals represent like parts throughout the various drawing figures, reference numeral 10 is directed to the hand tool device of the present invention. The device 10 (FIG. 1) receives high pressure fluid through an entrance 30 along arrow A, and discharges the fluid through an outlet 40 along arrow D. A rotor 90 (FIG. 2) is addressed by the high pressure fluid in a manner causing an output shaft 97 formed with the rotor 90 to rotate.

In essence, and with reference to FIGS. 1 through 5, the device 10 includes the following elements. The entrance 30 and outlet 40 are coupled to a housing 50 in a manner allowing high pressure fluid to pass into and out of the housing 50 through the entrance 30 and outlet 40. An insert 70 is nested within an interior of the housing 50. The insert 70 is shaped as a cylinder and receives an inlet port 74 and an exhaust port 76 formed in an end cap 75. The insert 70 is sized smaller than an interior of the housing 50 to frictionally fit therein.

The rotor 90 is rotatably supported within the cylindrical bore of the insert 70. The cylindrical bore provides a cavity for supporting the rotor 90 within the device 10. The rotor 90 includes a plurality vanes 92 pivotably supported by the rotor 90 so that the vanes 92 can pivot between a first position adjacent the rotor 90 to a second position pivoted away from the rotor 90. The rotor 90 is oriented with a rotational axis M offset from a central axis N of the cylindrical insert 70. This offset between the axis M and the axis N allows the vanes 92 to pivot between the first position and the second position as the rotor 90 rotates about arrow E.

High pressure fluid passing through the entrance 30 along arrow A has access to the inlet port 74. When the high pressure fluid enters the interior of the cylindrical insert 70 through the inlet port 74, the rotor 90 rotates about arrow E. Rotor 90 causes the output shaft 97 to rotate to perform useful work. The high pressure fluid is simultaneously decreased in pressure, passed through the exhaust port 76 and then exhausted out of the outlet 40 along arrow D. The cap 75 resides within an interior of the housing 50 adjacent a rear end 54 of the housing 50 and supports the entrance 30 and the outlet 40. The cap 75 supports one end shaft 99 of the rotor 90 within the housing 50 with its bore 71 supporting the shaft 99 attached to rotor 90 in an orientation along rotational axis M. The cap 75 abuts against cylinder 70. A coupler plug 200 fixes the cap 75 into the housing 50.

More specifically, and with reference to FIGS. 1 through 5, details of the entrance 30 and outlet 40 are described. The entrance 30 is preferably a hollow cylindrical conduit which extends a short distance perpendicularly away from the rear end 54 of the housing 50. The entrance 30 includes an exterior 32 which is substantially cylindrical and an interior 36 which is substantially cylindrical.

The outlet 40 is a hollow cylindrical construct extending substantially perpendicularly from the rear end 54 of the housing 50. The outlet 40 includes a cylindrical outer surface 42 concentric with a cylindrical inner surface 46.

Inlet 30 and outlet 40 are formed in a coupler plug 200 which abuts against rear end 54 of housing 50 and extends within the interior of the housing 50, holding cap 75 fixed. Plug 200 may be glued or sealed ultrasonically to the housing 50. Plug 200 includes a substantially cylindrical body 202 which leads to a flange 204 that seals housing 50. Flange 204 extends radially from body 202 and has a same outer diameter as the housing 50. Within the housing 50, the plug 200 decreases in diameter to frictionally reside within the housing via a stopper 206. An outer surface of stopper 206 includes a key 208 to orient the plug 200 and the inlet 30 and outlet 40. The key 208 aligns with a keyway 51 formed in the interior wall of housing 50. Threads T on body 202 and outside the housing 50 couples to a known threaded air line coupler (not shown) which will feed air to the device 10. A gasket G, formed as a disc and having inlet hole 31 and outlet hole 41 seal the air line coupler to the plug 200. Air is forced into inlet 30 and exhausted via outlet 40. Outlet 40 could be connected to a source of negative pressure (e.g. a vacuum) to define a push-pull system.

With reference now to FIGS. 2 through 6, details of the insert 70 are described. The insert 70 is preferably a substantially cylindrical hollow construct dimensioned to nest within the interior of the housing 50. The insert 70 defines a cylinder 72 on an interior thereof which is substantially circular in cross section. The insert 70 extends from the cap 75 forwardly to a necked-down portion of the housing 50 opposite the housing end 54 and terminates in an end wall 86 having a bearing opening 89 aligned with axis of rotor rotation M.

The cap 75 has a sleeve 61 which passes air from interior 36 to teardrop shaped inlet port 74 where an apex 63 of the teardrop "leads" the flow of air. Air flows more readily along arrow E (FIG. 6) because of the teardrop shape and its orientation promotes good contact with the rotor 90 to power the vane 92.

Similarly, air returning to the cap 75 first sees an exhaust opening 65 which is "banana" shaped (an elongate curved oval opening) which leads to outlet 40 via exhaust port 76. Exhaust opening 65 is several times (3–6) larger than the teardrop shaped opening 63 to further benefit from high air flow input and low air flow output. The cap 75 has a disc-shaped body potion 67 which fits within the housing 50 snugly. A stepped-down forward disc portion 69 fits within the cylindrical insert 70. The bore 71, which receives shaft 99 assures alignment of the openings and allows rotor rotation about axis M.

With reference now to FIGS. 2 through 9, details of the rotor 90 are described. The rotor 90 is sized to nest within the cylindrical insert 70. Rotor 90 includes a substantially rigid trunk 24 and a plurality of vanes 92 pivotably attached to the trunk 24 of the rotor 90. The rotor 90 preferably has an output shaft 97 integrally formed from the same material as the trunk 24 and vanes 92. Support shaft 99, also integral with trunk 24 and vanes 92 extend from the rotor 90 on an end opposite shaft 97 and is formed of like material. Shaft 99 acts as a bearing surface within bore 71 of cap 75. The trunk 24, shafts 97, 99 and vanes 92 can be formed of a plastic such as a polymeric hydrocarbon.

The trunk 24 includes a plurality of posts 93 extending away from the trunk 24. Each post 93 includes a hinge 94 on a trailing portion of an end thereof distant from the trunk 24 which supports a vane 92 thereon. A recess 26 is provided between adjacent posts 93. The recess 26 is shaped to allow one of the vanes 92 to be received within an adjacent recess 26 when sufficient force is applied to the vanes 92 to cause the vanes 92 to pivot about the hinge 94 to the trunk 24 as shown in figure 6. The recesses 26 are sufficiently deep to allow the vanes 92 to pivot down within the recesses 26. Each recess has a contact point 25 on the trunk which touches its vane 92. One or more points can be ground down in the mold to tune anomalies out of the mold cavity so as to balance the rotor.

Each vane 92 has a first nested position within the recess 26 and a second extended position pivoted out of the recess 26. Because of axis M, all vanes are in contact with the cylindrical wall 72. Tip 95 is on an end of the vane 92 remote from the hinge 94 and touches the wall 72 and provides a seal therebetween.

The hinges 94 are preferably inherently biased such that the vanes 92 are encouraged to extend out of the recesses 26 when no forces are applied which would force the vanes 92 into the recesses 26. This biasing is preferably programmed into the rotor 90 when the rotor 90 is formed. One method of forming the rotor 90 is through injection molding of an organic polymeric material where the vanes 92 and trunk 24 are formed simultaneously as a single unit within an injection mold. The hinge 94 is formed by providing a sufficiently thin portion of the mold which, in turn, thins and makes the hinge area which is defined as a narrow waisted flexible portion. Bending of the hinge material soon after forming the hinge 94 makes the hinge less brittle and more flexible. Forming the hinge 94 in its extended position promotes a natural outward bias. This method of manufacture greatly reduces the cost and complexity of the device 10, making it more economical for users to dispose of the device 10 after limited use, even a single use thereby promoting safety.

The rotor 90 is fabricated so that the natural position of the vanes 92 is extended out of the recess 26. In this way, each vane 92 is effectively "spring loaded" (i.e., programmed with a memory) and tends to retract out of the recess 26 at all times. The vanes 92 are preferably formed with a static position similar to the second position. This biasing of the vanes 92 toward the second position helps ensure that the vanes 92 maintain contact with the cylindrical wall 72, especially during start up when no centrifugal force is acting upon the vanes 92 and substantially all starting force comes through the teardrop opening 63 against a trailing portion of one vane. While biasing the vanes 92 is preferred, the rotor 90 can also self-start without biasing.

Viewed in FIG. 6, the rotor 90 preferably includes four identical regions, with each region including one vane 92. However, additional regions can be included. The trunk 24 is preferably substantially circular in cross-section.

Each vane 92 has a center of mass CM which affects a force with which the vanes 92 address the cylindrical wall 72. The location of the center of mass CM (FIG. 9) can be adjusted during molding to change a free speed of the rotor 90. For instance, the vanes 92 can be modified in geometry or weights such as higher density material can be added to portions of the vanes 92 during manufacture. Adjusting a location of the center of mass CM also alters a flywheel effect of the rotor 90. With the center of mass CM more distant from the hinge 94, a moment of inertia of the rotor 90 is altered. Also, adding or subtracting weight from the vanes 92 alters the inertia of the rotor 90. Each vane's 92 contact with the cylindrical wall 72 acts as a governor for the free speed of the rotor 90. By altering the mass and center of mass CM of the vanes 92, a speed at which the rotor 90 is governed can be altered as desired.

The output shaft 97 is sized to be rotatably supported within a bearing 89 of the cylindrical insert 70. The bearing 89 and journal 91 of shaft 97 thus interact to support the shaft 97 and the rotor 90. The output end 97 of the rotor 90 and bearing 89 are positioned to cause the rotor 90 to have its rotational axis M offset from the central axis N of the cylinder 70. This offset is preferably sufficient to still cause the vanes of the rotor 90 to always contact the cylindrical wall 72 of the insert 70. Thus, a distance between the rotational axis M of the rotor 90 and the central axis N of the cylinder 70 is equal to a radius of the cylinder 70 minus a radius that the posts 93 extend from the rotational axis M. This offset of the axes M, N causes the vanes 92 to, in essence, orbit a geometric center of the trunk 24 as the rotor 90 turns such that the vanes 92 have a perigee and an apogee opposite each other at 6 and 12 o'clock, FIG. 6.

Notice in FIG. 6 how the air inlet 74 and teardrop opening 63 coact with the vanes to open them. Each vane, even when fully closed exhibits a pocket P between the vane 92, post 93 and trunk 24. As the vane 92 extends open, an area of tangency between a flat vane wall 85 and contact point 25 of trunk 24 ceases. Also a flat wall 83 of the vane moves off a radial line. The vane includes an arcuate top wall 81 that meets radial wall 83 at tip 95. Tip 95 rides the inner wall 72 of insert 70. Insert 70, being asymmetrical, needs to be located in housing 50 and uses a rib 68 on an outer wall of the insert riding within a complemental groove 49 on an interior wall of the housing 50.

In use and operation, and with reference to FIGS. 3 through 5, details of the operation of the fluid reaction device 10 are described in detail. Initially, preferably high pressure fluid, such as air, is passed into the entrance 30 along arrow A. The fluid is preferably air, but can be another gas or can alternatively be incompressible fluid having a high or low pressure or velocity. The fluid then passes through the entrance hole 63 beyond inlet 74. The fluid passes around the rotor 90 causing the rotor 90 to turn about arrow E.

The rotor 90 is primarily caused to rotate due to a combination of the pressure caused by the high pressure and the offset of the rotor 90 within the cylinder 70. Other factors contributing to rotor 90 rotation can include a velocity of the fluid addressing the vane 92 of the rotor 90 and the ability of the fluid to expand within the cylinder 70. These other factors vary in importance from negligible to substantial depending on the specific configuration of the device 10 and the nature of the fluid utilized by the device 10. In general, incompressible fluids could provide high pressure, high velocity or both to cause rotor 90 rotation. Compressible fluids could provide high pressure, high velocity, expandability or a combination thereof to cause rotor 90 rotation. Torque exhibited by the rotor is maximized by allowing the total surfaces of the vanes 92 to be exposed to the drive fluid rather than just portions thereof as exhibited by prior art sliding vane rotors.

As the rotor 90 rotates along arrow E, the vanes 92 pivot about the hinge 94 along arrow G. This pivoting is caused by a combination of the biasing built into the hinge 94, centrifugal forces and fluid pressure tending to cause the vanes 92 to extend away from the rotational axis M of the rotor 90. In fact, if forces resist rotor 90 rotation, the vanes 92 are still caused to pivot due to the fluid pressure and torque is exhibited by the rotor 90. The high pressure fluid then comes into contact with outlet 65 and the exhaust port 76 where a pressure of the high pressure fluid is decreased. The fluid passes through the exhaust port 76. The fluid then passes out of the outlet 40 along arrow D. Rotation of the rotor 90 causes the output shaft 97 coupled thereto to rotate about arrow E (FIG. 2).

The tips 95 of the vanes 92 preferably remain in contact with the cylindrical wall 72 most of the time. This dragging of the tips 95 of the vanes 92 against the cylindrical wall 78 creates frictional forces which inhibit the rotor 90 from exceeding certain speeds. As the rotor 90 rotates faster and faster, a centrifugal force of the vanes 92 away from the rotor 90 increases, increasing a force that the vanes 92 exert normal to the cylindrical wall 72. In addition, pressure of the fluid against the vanes 92 increases a radially outward force against the cavity wall 72. This in turn increases a frictional force opposing rotation of the rotor 90, thus limiting speed. Because the vanes 92 pivot into contact with the wall 72, precise tolerances for the vane 92 dimensions need not be maintained during manufacture to provide an appropriate seal between the tips 95 and the wall 72.

Hence, the device 10 is provided with a maximum free speed at which frictional forces generated between the tips 95 of the vanes 92 of the rotor 90 are equal to rotational forces imparted against the vanes 92 of the rotor 90 by the differential pressure between a high inlet pressure and a low exit pressure. As long as a pressure differential exists between the high pressure inlet and low pressure exit and a seal is maintained so that fluid cannot pass directly from the inlet port 74 to the exhaust port 76 rotation will occur. With the vanes 92 remaining in contact with the cylindrical wall 72, a torque is applied about the rotational axis M of the rotor 90, encouraging the rotor 90 to rotate. The cylinder 70 and rotor 90 are configured such that a volume between adjacent vanes 92 and a pressure of fluid between the inlet port 74 and exhaust port 76 both remain substantially constant. Thus, adiabatic expansion of the fluid is kept to a minimum. This feature minimizes any thermal effect on the fluid or the device 10, which could otherwise alter the operating characteristics of the device 10.

Output shaft 97 has multiple drive facets 101. These facets 101 serve as a drive for a square socket 103 formed in a long gear 105. Long gear 105 includes a stop 107 which precludes axial translation. Stop 107 abuts against an interior barrier 111 within housing 50. Long gear 105 has a toothed end 109 remote from socket 103. Toothed end 109 meshes with a short gear 113 which has complemental teeth 115. Short gear 113 extends to an output shaft 117 to do work.

The housing 50 has a taper 119 forward the insert 70 as shown in FIGS. 1 through 4 and 10 through 11. The taper 119 connects to a snout 121 via a cone section 123 having knurling on the outside. A swivel extends therebetween and includes (FIG. 11) a rib 125 on a leading edge of the taper 119 is pressed into a groove 127 on a trailing portion of the cone 123 to allow swiveling about arrow F of FIG. 10.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A plastic, disposable rotary hand tool device receiving fluid as input and having a rotating shaft as output, comprising, in combination:

a rotor including an integrally formed substantially rigid trunk, a plurality of vanes, and a hinge means to pivotably attach said vanes to said trunk said vanes having a center of mass spaced from said hinge means;

a hollow cavity formed within a housing, said cavity including means to inlet fluid into said cavity parallel to an axis of rotor rotation, means to exhaust fluid out of said cavity, and means to rotatably support said trunk of said rotor within said cavity; and an output shaft coupled to said rotor such that when fluid enters said cavity, said shaft is caused to rotate, said housing having an output end with a bend, said housing having a swivel means adjacent said output shaft to allow reorientation of said housing with respect to said bend.

2. The device of claim 1 wherein said bend includes a first gear parallel to a long axis of said device and a second gear coupled to said first gear and skewed from said long axis.

3. The device of claim 2 wherein said means to rotatably support said rotor within said cavity includes a means to support said rotor with a rotational axis of said rotor spaced from a central axis of said hollow cavity.

4. The device of claim 3 wherein a seal point is provided between said rotor and said cavity, said seal point located between said inlet means and said exhaust means, said seal point defined by at least one portion of said rotor contacting said cavity between said inlet means and said exhaust means, whereby fluid passing through said inlet means and into said cavity is prevented from accessing said exhaust means by passing around a side of said rotor closest to said seal point.

5. The device of claim 4 wherein said rotor includes a recess adjacent each vane, each said recess having a contour which can receive an adjacent said vane therein when said vane is pivoted about said pivotable attachment means.

6. The device of claim 5 wherein said pivotable attachment means includes a hinge interposed between at least one of said vanes and said trunk, said hinge including means to apply a force causing extension of said vane out of an adjacent said recess.

7. The device of claim 6 wherein said inlet means includes at least one inlet port passing through said cavity, said inlet ports in fluid communication with a source of elevated pressure compressible fluid.

8. The device of claim 7 wherein said outlet means includes at least one outlet port passing through said cavity, said outlet ports in fluid communication with a region having lower pressure than said source of elevated pressure compressible fluid.

9. The device of claim 8 wherein said hollow cavity has an inside wall which exhibits a radius of curvature adjacent said seal point greater than a radius of said rotor when said vanes are collapsed against said trunk, and wherein said vanes include tips distant from said hinge, said tips of said vanes positioned to allow contact with said wall of said cavity at all times, whereby compressible fluid is prevented from passing from said inlet ports to said outlet ports without rotor rotation.

10. The device of claim 9 wherein said hollow cavity is defined by an insert nested within a substantially cylindrical housing, said insert having an outer diameter less than an inside diameter of said housing, whereby elevated pressure compressible fluid leaves a source of elevated pressure compressible fluid, passes through said entrance into said housing, through said inlet ports, around said rotor on a side of said rotor opposite said seal point causing said rotor to rotate, out of said exhaust ports, into said low pressure chamber, and exits said housing through said outlet, thereby converting elevated pressure compressible fluid into a combination of low pressure compressible fluid and rotor rotation.

11. The device of claim 9 wherein said trunk of said rotor includes a plurality of posts extending from said trunk, each said post including one of said hinges, each said vane having a shape which allows said vane to be pivoted into an adjacent said recess.

* * * * *